(12) United States Patent
Zong et al.

(10) Patent No.: US 12,186,742 B2
(45) Date of Patent: Jan. 7, 2025

(54) METHOD FOR REGULATING THE GAS VELOCITY OF THE EMPTY BED IN A FLUIDIZED BED

(71) Applicants: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

(72) Inventors: Hongyuan Zong, Shanghai (CN); Guozhen Qi, Shanghai (CN); Jing Cao, Shanghai (CN); Xiaohong Li, Shanghai (CN); Zhinan Yu, Shanghai (CN); Li Wang, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

(*) Notice: Subject to any disclaimer, the term of this patent is extended or adjusted under 35 U.S.C. 154(b) by 212 days.

(21) Appl. No.: 17/912,271

(22) PCT Filed: Sep. 16, 2020

(86) PCT No.: PCT/CN2020/115524
§ 371 (c)(1),
(2) Date: Sep. 16, 2022

(87) PCT Pub. No.: WO2021/184706
PCT Pub. Date: Sep. 23, 2021

(65) Prior Publication Data
US 2023/0139652 A1    May 4, 2023

(30) Foreign Application Priority Data

Mar. 19, 2020 (CN) .......................... 202010193664.X (51) Int. Cl.
*B01J 8/18* (2006.01)
*B01J 8/34* (2006.01)
(Continued)

(52) U.S. Cl.
CPC ........... *B01J 8/1809* (2013.01); *B01J 8/1827* (2013.01); *B01J 8/34* (2013.01); *B01J 29/85* (2013.01);
(Continued)

(58) Field of Classification Search
CPC . B01J 8/1809; B01J 8/1827; B01J 8/34; B01J 29/85; B01J 35/31;
(Continued)

(56) References Cited

U.S. PATENT DOCUMENTS 5,034,565 A * 7/1991 Harandi ................. C10G 50/00
                                                              585/722
7,790,941 B2   9/2010 Beech et al.
(Continued)

FOREIGN PATENT DOCUMENTS

| CN | 101094905 A | 12/2007 |
| CN | 101184709 A | 5/2008 |

(Continued)

OTHER PUBLICATIONS

International Search Report (PCT/ISA/210) with an English translation, and Written Opinion (PCT/ISA/237) mailed on Dec. 1, 2020, by the China National Intellectual Property Administration as the International Searching Authority for International Application No. PCT/CN2020/115524. (14 pages).
(Continued)

*Primary Examiner* — Ali Z Fadhel (74) *Attorney, Agent, or Firm* — Panitch Schwarze Belisario & Nadel LLP (57) ABSTRACT

The invention relates to a method for regulating the gas velocity of the empty bed in a fluidized bed, wherein solid catalysts are used as fluidized particles or as a part of fluidized particles, characterized in that the gas velocity of the empty bed $\mu$ of the reaction zone of the fluidized bed is measured, compared with the bed average catalyst density $\rho$ of the solid catalysts in the reaction zone of the fluidized bed, the gas velocity of the empty bed $\mu$ being adjusted as required such that the gas velocity of the empty bed $\mu$ and the bed average catalyst density $\rho$ satisfy the formula (I) below: $\rho=0.356\mu^3-4.319\mu^2-35.57\mu+M$; wherein M=250−; where $\mu$ is provided in m/s and $\rho$ is provided in kg/m$^3$. The method can be used for the industrial production of lower olefin.

20 Claims, 4 Drawing Sheets

(51) Int. Cl.
*B01J 29/85* (2006.01)
*B01J 35/31* (2024.01)
*C07C 1/24* (2006.01)

(52) U.S. Cl.
CPC ............... *B01J 35/31* (2024.01); *C07C 1/24* (2013.01); *B01J 2208/00663* (2013.01); *B01J 2208/0084* (2013.01); *B01J 2208/00929* (2013.01); *C07C 2529/85* (2013.01)

(58) Field of Classification Search
CPC ...... B01J 2208/00663; B01J 2208/0084; B01J 2208/00929; B01J 2208/00548; B01J 8/1818; C07C 1/24; C07C 2529/85; C07C 1/20; Y02P 30/20; Y02P 30/40
See application file for complete search history.

(56) References Cited

U.S. PATENT DOCUMENTS

| | | | |
|---|---|---|---|
| 9,403,735 | B2 | 8/2016 | Wei et al. |
| 2003/0105247 | A1* | 6/2003 | Braganca ............... C08F 10/02 526/61 |
| 2006/0147355 | A1 | 7/2006 | Beech, Jr. et al. |
| 2016/0048139 | A1* | 2/2016 | Samples ............... G06N 5/045 700/266 |
| 2016/0102032 | A1 | 4/2016 | Du et al. |
| 2016/0102033 | A1 | 4/2016 | Yang et al. |

FOREIGN PATENT DOCUMENTS

| | | |
|---|---|---|
| CN | 101328103 A | 12/2008 |
| CN | 102295505 A | 12/2011 |
| CN | 102295508 A | 12/2011 |
| CN | 102814151 A | 12/2012 |
| CN | 105214572 A | 1/2016 |
| CN | 105498647 A | 4/2016 |
| CN | 106795439 A | 5/2017 |
| EP | 0099690 A2 | 2/1984 |

OTHER PUBLICATIONS

Office Action issued on Apr. 29, 2023, by the National Intellectual Property Administration, China in corresponding Chinese Patent No. 202080098718.2 (9 pages).

Office Action issued on Jul. 13, 2023, by the Saudi Authority for Intellectual Property in corresponding Saudi Patent Application No. 522440571 (10 pages).

* cited by examiner

METHOD FOR REGULATING THE GAS VELOCITY OF THE EMPTY BED IN A FLUIDIZED BED

TECHNICAL FIELD

The invention relates to a method for regulating the air velocity of the empty bed in a fluidized bed and a process for preparing lower olefins by using the method.

BACKGROUND

Lower olefins, particularly ethylene and propylene, are important basic chemical raw materials, and the demand of the lower olefins is increasing. At present, the process of converting oxygenate through a fluidized bed reactor to olefin, especially the process of converting methanol to olefin (MTO) through a fluidized bed reactor is more and more interested.

In the MTO process, how to match the operating conditions of the fluidized bed reactor, including temperature, pressure, weight hourly space velocity, carbon deposition amount, and average catalyst density, etc., in the reaction zone, to achieve an optimal yield of the olefins, is a constant concern. For example, document CN101328103A discloses a process for converting methanol or dimethyl ether to lower olefins, which comprises feeding a raw material of methanol or dimethyl ether into a reaction zone of a fluidized bed reactor, and contacting the raw material with a catalyst comprising a silicoaluminophosphate molecular sieve; wherein the average density of the reaction zone is 20-300 kg/m$^3$, and the average coke deposition amount of the catalyst in the reaction zone is 1.5-4.5% by weight, under the conditions of a gauge pressure of 0.05-1 MPa, an average temperature of the reaction zone of 450-550° C., and an average superficial gas velocity of the reaction zone of 0.8-2.0 m/s. The carbon-based selectivity of the lower olefin reaches up to 81.51 wt %.

However, with the increasing demand of ethylene and propylene in the market, higher requirements are raised on the production technology of the lower olefins.

When a fluidized bed reactor is used for production (for example, production of lower olefins), the operating pressure and space velocity of the fluidized bed reactor are important parameters. For example, in a process for producing lower olefins from methanol, since the reaction of converting methanol to lower olefins is a molecular enhancement reaction, increasing the reaction pressure generally results in a decrease in both the conversion rate of methanol and the selectivity to lower olefins, and therefore, in general, the MTO process is selected to perform the reaction at a low pressure (e.g., less than 0.2 MPa). With the increasing demand of the market for lower olefins, the MTO process is inevitably large-scaled. By increasing the input of raw materials according to a certain proportion and simultaneously increasing the pressure and the gas velocity of the fluidized bed reactor, the technicians can easily achieve the purpose of increasing the productivity of the lower olefins. However, according to the prior art, for manufacturers, after the pressure and the space velocity are increased, although the productivity of the lower olefins is increased, the efficiency of converting the methanol into the target product is correspondingly reduced, so that the material consumption of the methanol is increased, and the method is not necessarily cost-effective from the economic point of view. On the other hand, after the pressure and the space velocity are increased, more catalyst particles are suspended in the dilute phase section of the reactor, and as the processing capacity of the cyclones is limited, product gas carries more catalysts out of the reactor system, so that the loss of the catalysts is increased, and the catalyst inventory in the reactor is continuously reduced and the load of the catalysts is increased over time, so that the yield of the target product converted from methanol is influenced.

SUMMARY OF THE INVENTION

The inventors of the present invention discover that, under the conditions of higher reaction pressure and space velocity, both high methanol conversion and high selectivity to lower olefins can be ensured by regulating the relationship between the superficial gas velocity μ in the reaction zone of the fluidized bed reactor and the average catalyst density ρ in the reaction zone (in the context of the present invention, for convenience, the "average catalyst density in the reaction zone" is used interchangeably with the "bed average catalyst density" and the "bed density"). The present invention has been completed based on these discoveries.

Specifically, the present invention relates to the following aspects:

1. A method for regulating the superficial gas velocity in a fluidized bed, wherein solid catalysts are used as the fluidized particles or as a part of the fluidized particles, characterized in measuring the superficial gas velocity μ of the reaction zone of the fluidized bed, comparing it with the bed average catalyst density ρ of the solid catalysts in the reaction zone of the fluidized bed, adjusting the superficial gas velocity μ as needed so that the superficial gas velocity μ and the bed average catalyst density ρ satisfy the formula (I) below:

$$\rho = 0.356\mu^3 - 4.319\mu^2 - 35.57\mu + M \quad (I)$$

wherein M=250-554, preferably 300-550, or 400-500, such as 487.9;

μ is provided in m/s and ρ is provided in kg/m$^3$.

2. The method of aspect 1 or any other aspect of the invention, wherein the bed has an average catalyst density of 200 to 500 kg/m$^3$, preferably 250 to 450 kg/m$^3$, more preferably 300 to 430 kg/m$^3$.

3. The method according to aspect 1 or any other aspect of the invention, wherein baffle components $B_j$ (1) are provided within the reaction zone of the fluidized bed, the number of layers of the baffle components (1) being independently in each case m, m being a value varying between 1 and 10; and the distance between two adjacent baffle components $B_j$ (1) is $H_j$, each $H_j$ being independently 0.2-1 times of the diameter D of the fluidized bed reaction zone, wherein j=1–m;

the baffle component $B_j$ (1) comprises a plurality of rib plates (7), and the arrangement of the rib plates (7) is one of radial arrangement (A), spiral arrangement (B1-B2) and dendritic arrangement (C1-C3);

when the baffle component $B_j$ (1) is projected on the cross section of the reaction zone of the fluidized bed, the cross section area not occupied by the projection accounts for 70-95% of the cross section area of the reaction zone of the fluidized bed; and the distance between the outermost edge of any baffle component $B_j$ (1) and the reaction zone cylinder wall (2) of the fluidized bed is each $h_1$; and $h_1$ is independently 0.005 to 0.05 times the diameter D of the reaction zone of the fluidized bed.

4. The method according to aspect 3 or any other aspect of the invention, wherein baffle components $B_j$ (1) in the radial arrangement (A) or spiral arrangement (B1-B2) comprise rib plates (7) and positioning rings $R_i$ (6); the positioning rings $R_i$ (6) are coaxially arranged; the rib plates (7) are connected with the positioning rings $R_i$ (6) and are uniformly distributed along the circumferential direction, wherein:

(a) the number of the positioning rings $R_i$ (6) is n independently, wherein n is a value varying from 1 to 10, and i=1 to n; and the n positioning rings $R_i$ divide the reaction zone of the fluidized bed into n+1 rib plate ring layers which are coaxial in the radial direction, each rib plate ring layer being represented by $L_g$, and g=1 to (n+1); and (b) the number of the rib plates (7) of each rib plate ring layer is p, the number of the rib plates (7) in the g-th rib plate ring layer $L_g$ is $p_g$, and the range for $p_g$ is (3–10)×g.

5. The method according to aspect 3 or 4 or any other aspect of the invention, wherein the baffle components (1) in spiral arrangement (B1-B2) has an angle α between the tangent of the outer curvature of the rib plate (7) and the radial direction, α being 10-80°.

6. The method according to aspect 3 or any other aspect of the invention, wherein the baffle components $B_j$ (1) in dendritic arrangement (C1-C3) are formed of a plurality of main rib plates (4) and a plurality of auxiliary rib plates (5); the number of the main rib plates (4) on each baffle component $B_j$ (1) is k independently, and k is 2-8; the main rib plates (4) and the auxiliary rib plates (5) are perpendicularly arranged in a crossed manner; and the total number of the auxiliary rib plates (5) on each baffle component $B_j$ (1) is q independently, and q is 10-40.

7. The method according to aspect 6 or any other aspect of the invention, wherein the baffle component $B_j$ (1) in dendritic arrangement has a type I dendritic arrangement (C1) in which two of the plurality of the main rib plates (4) are each $D-2 \times h_1$ in length and are perpendicular to each other, which are referred to as a first main rib plate and a perpendicular main rib plate, respectively; the other main rib plates (4) in the plurality of main rib plates (4) are arranged in parallel with the first main rib plate, with a same spacing distance $h_4$; the auxiliary rib plates (5) on each main rib plate (4) are arranged in parallel, with a same spacing distances $h_2$; a pair of auxiliary rib plates on the first main rib plate, which are closest to the perpendicular main rib plate, are respectively spacing from the perpendicular main rib plate by a distance $h_2$, a pair of auxiliary rib plates on two main rib plates adjacent to the first main rib plate, which are respectively closest to the perpendicular main rib plate, are respectively spacing from the perpendicular main rib plate by a distance $\frac{1}{2}h_2$, and the auxiliary rib plates (5) on the interval main rib plates (4) are aligned on a straight line in the longitudinal direction; and the distance $h_3$ between the ends of the auxiliary rib plates (5) on the interval main rib plates (4) is (0.01-0.2) times of $(D-2 \times h_1)/k$.

8. The method according to aspect 6 or any other aspect of the invention, wherein the baffle component $B_j$ in dendritic arrangement has a type II dendritic arrangement (C2-C3), wherein the main rib plates (4) of the baffle components (1) are arranged crosswise and uniformly arranged circumferentially with a length of $D-2 \times h_1$; the number of the auxiliary rib plates (5) on each main rib plate (4) is the same, the auxiliary rib plates are arranged in parallel with a same spacing distance $h_5$; the auxiliary rib plates (5) on each main rib plate (4) form sector areas, and the distance $h_6$ between the sector areas is 0.5-3 times of $h_1$.

9. The method according to aspect 3 or 4 or any other aspect of the invention, wherein the rib plate (7) is in any one of π-shape (D1-D4), inverted V-shape (D5), inclined plate-shape (D6) and arc-shape (D7); the rib plate (7) is provided with small holes (10); the small holes (10) are in any one of circle, ellipse, rectangle, triangle, polygon and the like shape; and the rib plate (6) in π-shape (D1-D4) comprises a rib plate flank (9) and a rib plate top (8).

10. The method according to aspect 9 or any other aspect of the invention, wherein the width l of the rib plate (7) is (0.2-0.9) times of $(D-2 \times h_1)/(p$ or $q)$ and the height δ of the rib plate (7) is (0.1-0.6) times of the width l of the rib plate (7).

11. The method according to aspect 9 or any other aspect of the invention, wherein the width $l_1$ of the rib plate top (8) of the rib plate (6) in π-shape (D1-D4) is (0.1-0.5) times of the width l of the rib plates (7); the height $δ_1$ of the rib top (8) of the rib plate (6) in π-shape (D1 and D3) is 0.05-0.3 times of the height δ of the rib plate (7).

13. The method according to aspect 3 or 4 or any other aspect of the present invention, characterized in that the angle of the baffle component (1) to the cross-section of the fluidized bed reaction zone is from −25 to 60°, preferably −20 to 50°, more preferably −15 to 40°.

14. The method according to aspect 1 or any other aspect of the invention, characterized in providing a control value M' for a control range within ±5%, preferably ±2%, or ±1%, or ±0.5% from a setpoint value of M, wherein when no control value M' is present within the control range of the setpoint value M such that the superficial gas velocity μ and the bed density ρ satisfy the formula (I), the setpoint value M is brought into the formula, a calculated value of the corresponding superficial gas velocity μ is calculated from the bed density ρ accordingly, and the superficial gas velocity is adjusted in accordance with the calculated value.

15. A process for producing lower olefins, comprising the step of contacting an oxygenate feedstock with molecular sieve catalysts in a fluidized bed reaction zone, to generate lower olefins under effective conditions; characterized in that in the fluidized bed reaction zone, the superficial gas velocity μ and the bed average catalyst density ρ satisfy the formula (I) below:

$$\rho = 0.356\mu^3 - 4.319\mu^2 - 35.57\mu + M \quad (I);$$

wherein, M=250-554, preferably 300-550, or 400-500, such as 487.9;

μ is provided in m/s and ρ is provided in kg/m³; or when the superficial gas velocity μ and the bed average catalyst density ρ do not satisfy formula (I), the superficial gas velocity is adjusted by the method according to aspect 1 or any other aspect of the invention so as to lead the superficial gas velocity μ and bed average catalyst density ρ to satisfying formula (I).

16. The process for producing lower olefins according to aspect 15 or any other aspect of the present invention, characterized in that the effective conditions comprise: a top pressure of the reactor of more than 0.1 MPa, preferably 0.2-1 MPa; a reaction temperature of more than 400° C., preferably 450-500° C.

17. The process for producing lower olefins according to any one of aspects 15 to 16 or any other aspect of the present invention, characterized in that the oxygenate feedstock comprises methanol; the molecular sieve is a silicoaluminophosphate molecular sieve, preferably SAPO-18, SAPO-34, SAPO-5 or a combination thereof.

TECHNICAL EFFECTS

According to the process of the present invention, the reaction zone throughput is increased.

According to the process of the present invention, not only high conversion of raw materials can be ensured, but also high selectivity to the lower olefins can be ensured, where the selectivity to the lower olefins (ethylene and propylene) can reach 83% or more.

EMBODIMENTS OF THE INVENTION

The present invention will be further illustrated in more detail below, while it should be understood that the scope of the invention is not restricted by the embodiments, but is defined by the appended claims.

All publications, patent applications, patents, and other references mentioned in this specification are herein incorporated by reference in their entirety. Unless defined specifically, all technical and scientific terms used herein have the same meaning as commonly understood by those skilled in the art to which this invention belongs. In case of conflict, the present specification, including definitions, will control.

When the present specification mentions a material, substance, method, step, device, or component, etc. with the derivative words "known to those skilled in the art", "prior art" or the like, the term derived is intended to cover those conventionally used in the field of the present application, but also cover those that are not currently known, whilst will become known in the art to be useful for the similar purposes.

In the context of the present specification, the term "fluidized bed reaction zone" is used in reference to a fluidized bed reactor. Desirably, a fluidized bed reactor includes a reaction zone, an inlet zone, and a separation zone. The "inlet zone" is a zone in the reactor through which the feedstock and catalyst are fed. The "reaction zone" is a zone in a reactor where the feed is contacted with the catalyst under conditions effective to convert the oxygenate of the feed to lower olefin products. The "separation zone" is a zone in the reactor where the catalyst and any other solids within the reactor are separated from the product. Typically, the reaction zone is located between the inlet zone and the separation zone.

In the context of the present specification, the term "superficial gas velocity" is used to refer to the gas linear velocity calculated as empty bed. The calculation method comprises: assuming the gas-solid flow being plug flow, dividing the gas volume flow rate in unit time under the actual reaction conditions in the reaction zone by the cross-sectional area of the reaction zone.

In the context of the present specification, the term "space velocity" is used to refer to the weight flow rate of the feed divided by the total weight of catalyst in the reaction zone in $h^{-1}$.

In the context of the present specification, the term "bed average catalyst density" is used and is calculated as the total weight of catalyst in the reaction zone divided by the volume of the reaction zone.

In the context of the present specification, the coke deposition amount (or average coke deposition amount) of the catalyst is calculated by the weight of coke deposit on the catalyst divided by the weight of the catalyst. The method for measuring the weight of the coke deposit on the catalyst comprises the following steps: weighing 0.1-1 g of the carbon-carrying catalyst, placing the catalyst in a high-temperature carbon analyzer for combustion, and measuring the weight of carbon dioxide generated by combustion through infrared rays, to provide the weight of coke deposited on the catalyst. In order to determine the coke deposition amount of the catalyst in the reaction zone, aliquots of the catalyst in small equal amounts may be withdrawn continuously or periodically from various locations in the reaction zone.

In the context of the present specification, when the invention is applied to a methanol to olefin reaction, the term "carbon-based yield" used is calculated as the weight of product obtained per unit time divided by the weight of $CH_2$ feed in the methanol molecule.

All percentages, parts, ratios, etc. involved in the present specification are indicated by weight and pressures are gauge pressures unless explicitly indicated otherwise.

In the context of the present specification, in case of keeping the reactor size unchanged, a superficial gas velocity desired is achieved by adding an inert medium (such as steam, etc.) when the velocity cannot be achieved by the feedstock processing scale without changing the reactor size.

In the context of this specification, any two or more embodiments of the invention may be combined to form an embodiment, and the resulting embodiment is a part of the original disclosure of this specification, and is within the protection scope of the invention.

In one embodiment, the present invention provides a method of regulating the superficial gas velocity in a fluidized bed, wherein solid catalysts are used as the fluidized particles or as a part of the fluidized particles, characterized in measuring the superficial gas velocity μ of the fluidized bed reaction zone, comparing it with the bed average catalyst density ρ of the solid catalysts in the fluidized bed reaction zone, adjusting the superficial gas velocity μ as needed such that the superficial gas velocity μ and the bed average catalyst density ρ satisfy the formula (I) below:

$$\rho = 0.356\mu^3 - 4.319\mu^2 - 35.57\mu + M \qquad (I)$$

wherein M is a setpoint, being a numerical value within the range of 250-554, preferably 300-550, or 400-500, or 450-500, such as 480, 481.8, 482.5, 483, 484.4, 485, 486, 487, 487.5, 487.9, 488, 488.3, 489, or 490; μ is provided in m/s and ρ is provided in kg/m³.

In one embodiment, for the actual fluidized bed operation, for example for a given catalyst and reactor, the bed density ρ is determined accordingly, whereby the desired superficial gas velocity μ is calculated according to formula (I). The thus obtained numeric point of µ is used as a target setpoint for the superficial gas velocity, to adjust the actually operated superficial gas velocity. Here, the specific method of regulating the superficial gas velocity in accordance with the target setpoint is not particularly limited, for example, by regulating the opening degree of a valve, regulating the output of a pump or a compressor, or the like.

In fluidized bed operation, both the superficial gas velocity µ and the bed average catalyst density ρ may fluctuate over time. For example, the bed average catalyst density, ρ, involved in the present invention is calculated as the total weight of the catalysts in the reaction zone divided by the volume of the reaction zone, whereas it is known that as the fluidized bed is operated, the total amount of catalyst in the reaction zone may decrease, thereby causing a decrease in ρ. For another example, the superficial gas velocity µ may vary due to feed instability, etc.

Accordingly, for a given setpoint of M, variations in ρ and/or µ may cause frequent adjustments to the fluidized bed in order to satisfy formula (I). Without being limited by any known theory, it is believed that in the actual operation of a fluidized bed, it is useful to give a control value M' which lies within a control range of the M setpoint, which is, for example, within a range of ±5%, preferably ±2%, or ±1%, or ±0.5% from the M setpoint, but unnecessary to be symmetrically arranged with respect to the setpoint. For example, for a M setpoint of 487, the control range may be, for example, 480-495, such as 482-490, 485-492, 486-489 and the like. Thus, for a given M setpoint, it is not necessary to immediately adjust the superficial gas velocity µ as long as there can be a control value M' existing within the control range of the setpoint M to allow the superficial gas velocity µ and the bed density ρ satisfy the formula (I). When no control value M' is available in the control range of the setpoint M can allow the superficial gas velocity µ and the bed layer density ρ meet the formula (I), the setpoint M is brought into the formula, a corresponding calculated value of the superficial gas velocity µ is calculated according to the bed layer density ρ at the moment, and the superficial gas velocity is adjusted according to the calculated value.

Without being limited by any known theory, it is believed that the provision of the baffle components (1) in the reaction zone of the fluidized bed helps to achieve the regulation such that the superficial gas velocity µ and the bed density ρ can satisfy the formula (I). In various embodiments, the number of layers of the baffle components (1) is in each case independently m, m being a value varying between 1 and 10.

For a reactor having m layers of the baffle components (1), each layer of the baffle components (1) is represented by $B_j$, j=1~m. The distance between two adjacent baffle components $B_j$ and $B_{j-1}$ is referred to as it, wherein the distance between the lowermost baffle component $B_1$ (1) and the methanol feed distributor (a distribution plate) is defined as $H_1$, then the ratio of $H_1$ to the reaction zone height is 0.1-0.4, such as 0.2-0.3, such as 0.25, while each of the other $H_j$ is independently 0.2-1 times of the fluidized bed reaction zone diameter D. In one embodiment, each it, except $H_1$, is the same. In one embodiment, the fluidized bed reaction zone preferably has a circular or substantially circular cross-section. In one embodiment, adjacent two baffle components $B_j$ (1) are staggered or stacked with one on top of the other. The baffle component $B_j$ (1) comprises a plurality of rib plates (7), and the arrangement of rib plates (7) is one of radial arrangement (A), spiral arrangement (B1-B2), and dendritic arrangement (C1-C3). The arrangement of the plurality of rib plates (7) of each layer of the baffle component $B_j$ (1) is the same or different. When the baffle component $B_j$ (1) is projected onto the cross-section of the reaction zone of the fluidized bed, the cross-sectional area not occupied by the projected area is 70% to 95% of the cross-sectional area of the reaction zone of the fluidized bed. The distance between the outermost edge formed by any baffle $B_j$ (1) and the wall surface (2) of the reaction zone cylinder of the fluidized bed is $h_1$; and in various embodiments, $h_1$ is independently a value between 0.005 and 0.05 times of the diameter D of the reaction zone of the fluidized bed. That is, the connecting line of the outermost edges of all the baffle components $B_j$ (1) constitutes a pattern having a hydraulic diameter of (D−2×$h_1$); and when the fluidized bed reaction zone preferably has a circular cross section, the outermost edge of all of the baffle components $B_j$ (1) forms a pattern having a circular shape with a diameter of (D−2×$h_1$).

Figure 2:
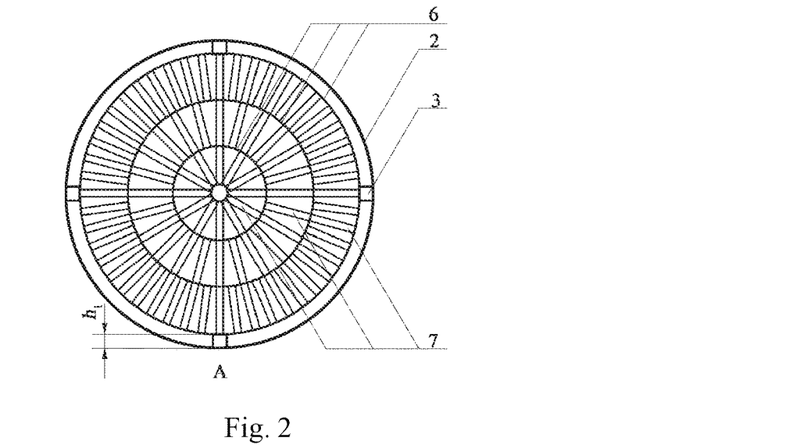
FIG. 2 illustrates a baffle component in radial arrangement (A) useful in the method of the present invention.
Figure 3A:
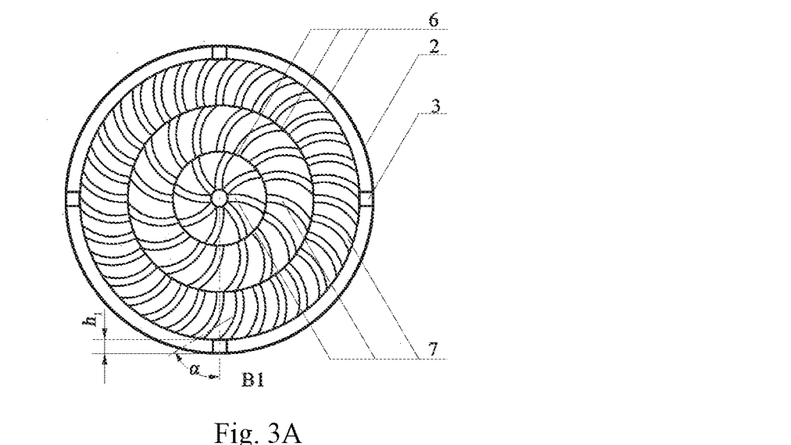
FIGS. 3A-B illustrate a baffle component in spiral arrangement (B1-B2) useful in the method of the invention.
Figure 3B:
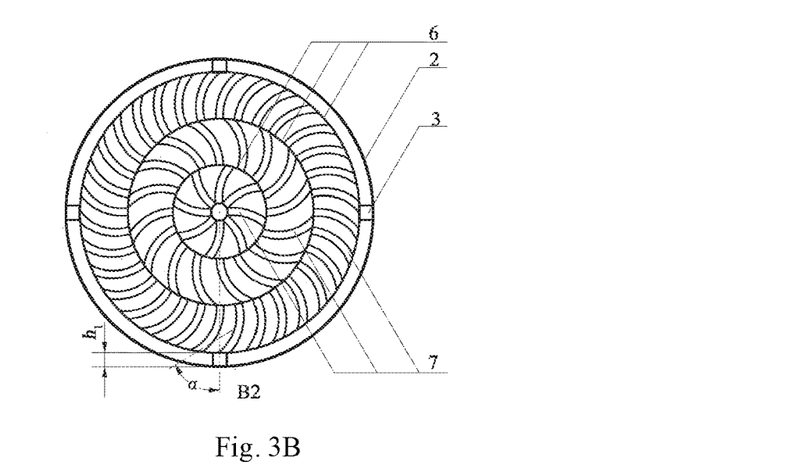

In one embodiment, referring to FIG. 2 and FIGS. 3A and 3B, baffle components $B_j$ (1) in the radial arrangement (A) or spiral arrangement (B1-B2) comprise rib plates (7) and positioning rings $R_i$ (6). In one embodiment, the positioning rings $R_i$ (6) are coaxially arranged; the rib plates (7) are connected with the positioning rings $R_i$ (6) and are uniformly distributed along the circumferential direction, wherein:

(a) in each embodiment, the number of the positioning rings $R_i$ (6) is n independently, n is a value varying between 1 and 10, each layer of positioning rings (6) is represented by $R_i$, and i=1 to n, wherein $R_1$ represents the radially innermost positioning ring, and $R_n$ represents the radially outermost positioning ring; the n positioning rings $R_i$ divide the reaction zone of the fluidized bed into n+1 rib plate ring layers which are coaxial in the radial direction, each rib plate ring layer is represented by $L_g$, and g=1 to (n+1), wherein $L_1$ is a rib plate ring layer at the innermost side in the radial direction, and $L_{n+1}$ is a rib plate ring layer at the outermost side in the radial direction; and (b) the number of the rib plates (7) of each rib plate ring layer is p, the number of the rib plates (7) in the g-th rib plate ring layer $L_g$ is $p_g$, and the range for the $p_g$ is (3-10)×g.

In one embodiment, baffle components $B_j$ (1) in the radial arrangement (A) or spiral arrangement (B1-B2) do not comprise a positioning ring. In this embodiment, the number of the rib plates (7) is 3 to 10.

In one embodiment, referring to FIG. 2, all the baffle components $B_j$ (1) are in the same radial arrangement (A) for a given reactor.

In one embodiment, referring to FIGS. 3A and 3B, the angle between the tangent of the outer curvature of the rib plate (7) of the baffle component (1) in spiral arrangement (B1-B2) and the radius direction is α, which α is from 10 to 80°. When the baffle component $B_j$ (1) comprises a positioning ring $R_i$ (6), the g-th rib ring layer of the baffle component (1) in spiral arrangement (B1-B2) and the rib plate (7) of the (g+1)-th rib ring layer can be arranged in the same direction or in opposite directions, wherein the arrangement in the same direction or in opposite directions means a clockwise (right-hand) or counterclockwise (left-hand) spiral, respectively, as seen in a top view of the rib plate (7). Preferably, in one embodiment, referring to FIGS. 3A and 3B, all baffle components $B_j$ (1) are arranged in the same spiral arrangement (B1-B2) for a given reactor.

Figure 4A:
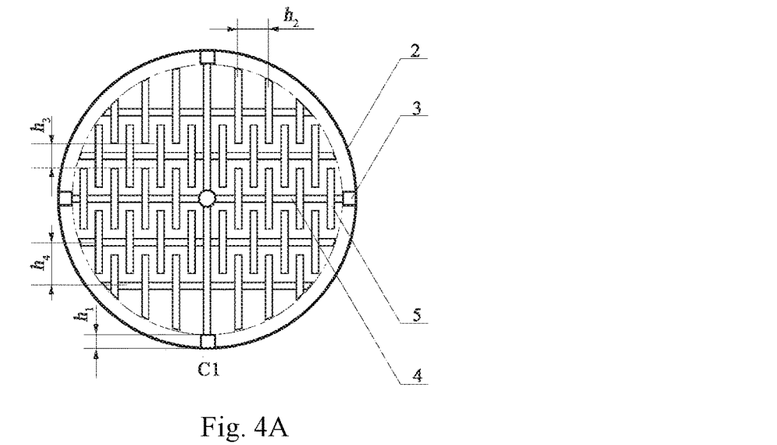
FIGS. 4A-C illustrate a baffle component in dendritic arrangement (C1-C3) useful in the process of the present invention.
Figure 4B:
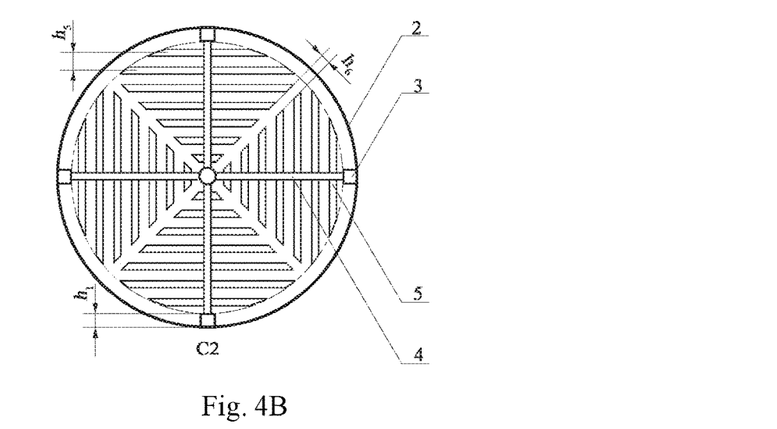
Figure 4C:
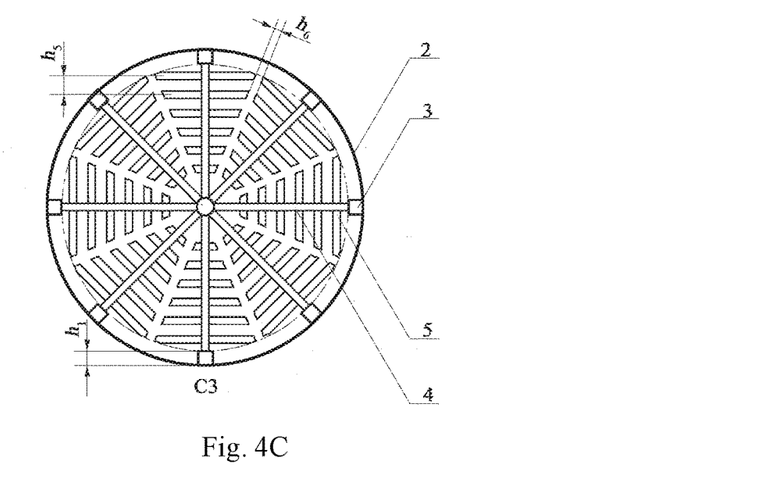

In one embodiment, referring to FIG. 4A-4C, baffle components $B_j$ (1) in dendritic arrangement (C1-C3) have rib plates (7) consisting of a plurality of main rib plates (4) and a plurality of auxiliary rib plates (5). In various embodiments, the number of the main rib plates (4) is k independently, k being 2-8. The main rib plates (4) and the auxiliary rib plates (5) are perpendicularly arranged in a crossed manner and are in a dendritic shape. In various embodiments, the number of auxiliary rib plates (5) on each baffle component $B_j$ (1) is independently q, q being 10-40. The numbers of the main rib plates (4) on every two baffle components $B_j$ (1) are the same or different. In one embodiment, the number of the main rib plates (4) on each baffle component $B_j$ (1) is the same. The numbers of the auxiliary rib plates (5) on every two main rib plates (4) are the same or different.

In one embodiment, referring to FIG. 4A, the baffle component $B_j$ (1) in dendritic arrangement has a type I dendritic arrangement (C1), which type I dendritic arrangement (C1) denotes where two of the plurality of main rib plates (4) each being $(D-2 \times h_1)$ in length are perpendicular to each other, referred to as the first main rib and the perpendicular main rib, respectively. In other words, when the connecting line of the outermost side edge of the baffle components $B_j$ (1) constitutes a circle (or a substantial circle), the lengths of the first main rib and of the perpendicular main rib are each equal to the diameter of the circle (or the substantial circle) constituted by the connecting line. The other main rib plates (4) of the plurality of main rib plates (4) are arranged in parallel with the first main rib, are continuous in the longitudinal direction of each main rib, and have the same interval $h_4$. A plurality of the auxiliary rib plates (5) on each main rib plate (4) are arranged in parallel, having a same interval $h_2$, and the auxiliary rib plates each extend, in the longitudinal direction, to a position spacing $h_0$ ($h_0 > 0$, not shown in the figure) from the main rib plate, within in the space defined by one main rib plate and two adjacent main rib plates; or for the outer main rib, each of the plurality of auxiliary rib plates (5) thereon extends in the longitudinal direction between the connecting line from the one of the adjacent main rib plates to the connecting line of the outermost edge of all the baffle components $B_j$ (1). The pair of (two) auxiliary rib plates on the first main rib closest to the perpendicular main rib are positioned spacing from the perpendicular main rib by a distance $h_2$, and the pairs of (4 in total) auxiliary rib plates on each of two main rib plates adjacent to the first main rib closest to the perpendicular main rib are positioned spacing from the perpendicular main rib by a distance $\frac{1}{2}h_2$. In one embodiment, the auxiliary rib plates (5) on two interval main rib plates (4) are aligned (in a straight line) in the longitudinal direction. In the context of the present invention, the "interval" relationship of the rib plates means that there is only one other rib of the same type and in the same arrangement between the two rib plates involved; for example, referring to FIG. 4A, two of 3 adjacent parallel main rib plates separated by a middle main rib are referred to as "interval" main rib plates. The spacing in the longitudinal direction of every two adjacent auxiliary rib plates (5) on the interval main rib plates (4) is referred to as the inter-end distance $h_3$, and each two adjacent auxiliary rib plates (5) have the same inter-end distance $h_3$ which is in each case independently a value between (0.01-0.2) times of $(D-2 \times h_1)/k$. Accordingly, when a main rib plate (4) of width l is used, $h_3 = 2h_0 + l$. Preferably, in one embodiment, referring to FIG. 4A, all baffle components $B_j$ (1) adopt the same type I dendritic arrangement for a given reactor (C1).

In one embodiment, referring to FIGS. 4B and 4C, the component $B_j$ in dendritic arrangement has a type II dendritic arrangement (C2-C3), wherein the type II dendritic arrangement (C2-C3) means that the main rib plates (4) of the baffle component (1) are arranged in a crossed manner and are uniformly arranged in the circumferential direction, and the length of each main rib is $D-2 \times h_1$. The number of the auxiliary rib plates (5) on each of the main rib plates (4) is the same. The auxiliary rib plates (5) on each main rib plate (4) are arranged parallel to each other and have the same spacing $h_5$. The connecting line formed by the outermost side edge of the auxiliary rib plates (5) on each main rib plate (4) and the outermost side of the main rib forms a sector area. For a same baffle component $B_j$ (1), the sector-shape areas formed by the auxiliary rib plates (5) on each main rib plate (4) have equal spacing $h_6$, which is 0.5-3 times of $h_1$ independently in each case. Preferably, in one embodiment, referring to FIGS. 4B and 4C, all baffle components $B_j$ (1) adopt the same type II dendritic arrangement (C2-C3) for a given reactor.

Without being limited by any known theory, in one embodiment, it is believed that the plurality of the baffle components $B_j$ (1) may be in the form of a combination of several of radial arrangement (A), spiral arrangement (B1-B2), and dendritic arrangement (C1-C3).

Figure 5:
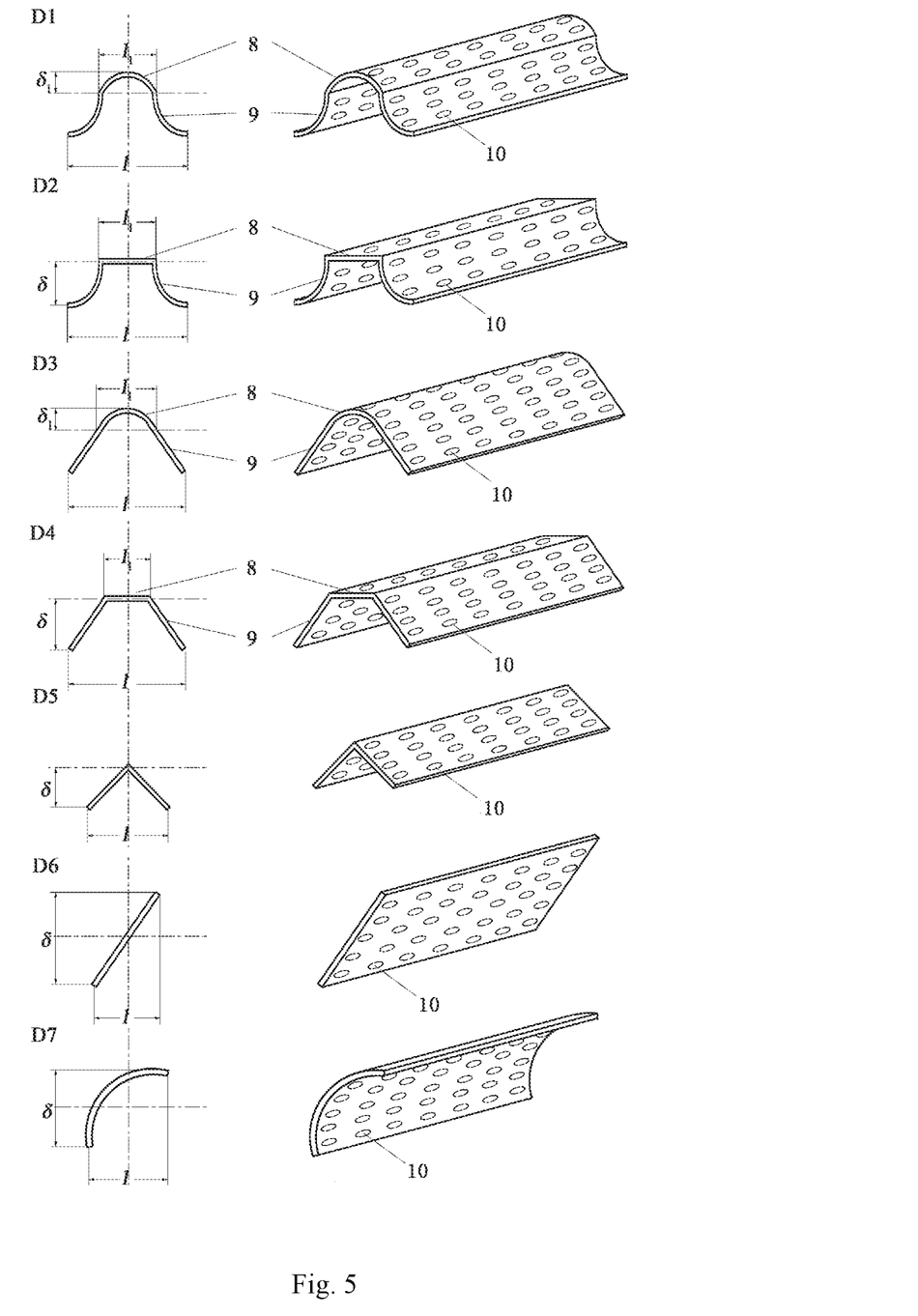
FIG. 5 illustrates a rib useful in the baffle component of the present invention.

In one embodiment, referring to FIG. 5, the rib plate (7) is in any one of π-shape (D1-D4), inverted V-shape (D5), inclined plate-shape (D6) and arc-shape (D7). The rib plate (7) is provided with small holes (10); which small holes (10) are in any shape one of circle, ellipse, rectangle, triangle, polygon and the like. The rib plate (6) in π-shape (D1-D4) comprises a rib plate flank (9) and a rib plate top (8). In one embodiment, the arrangement and the opening rate of the small holes and the like are not particularly limited, as long as they satisfy the aforementioned and later-described various requirements with respect to the rib plate (7) and the baffle component $B_j$ (1), and particularly, for example, such that when the baffle component $B_j$ (1) is projected on the cross-section of the reaction zone of the fluidized bed, the cross-sectional area not occupied by the projection accounts for 70% to 95% of the cross-sectional area of the reaction zone of the fluidized bed.

Referring to FIG. 5, the π-shape rib plate (7) in the form of D1 is a rib having an upwardly convex arc-shape top (8) and arc-shape flanks (9); the π-shape rib plate (7) in the form of D2 is a rib having a flat top (8) and arc-shape flanks (9); the π-shape rib plate (7) in the form of D3 is a rib having an upwardly convex arc-shape top (8) and flat flanks (9); and the π-shape rib plate (7) in the form of D4 is a rib having a flat top (8) and flat flanks (9). With reference to FIG. 5, for π-shape rib plates (7) in the D1 and D2 forms, the arc-shape flank is "concave" relative to the inside space of the closed figure formed by the projection shape, being an orthographic projection of the π-shape rib plate (7) over the length of the rib, and by the end connecting lines of the flanks.

In one embodiment, referring to FIG. 5, the width l of the rib plate (7) is (0.2-0.9) times of $(D-2 \times h_1)/(p$ or $q)$, and the height δ of the rib plate (7) is (0.1-0.6) times of the width l of the rib plate (7); wherein the width l of the rib plate (7) refers to the width of the rib as projected in the cross section of the reactor when the rib is installed in the reactor; and the height δ of the rib plate (7) refers to the height of the rib as projected in the axial direction of the reactor when the rib is installed in the reactor.

In one embodiment, the width $l_t$ of the rib top (8) of the rib plate (6) in π-shape (D1-D4) is (0.1-0.5) times of the width l of the rib plate (7); the height $δ_1$ of the rib top (8) of the rib plate (6) in π-shape (D1 and D3) is (0.05-0.3) times of the height δ of the rib plate (7); wherein the width $l_t$ of the rib top (8) refers to the width of the rib top (8) as projected in the cross section of the reactor when the rib is installed in the reactor; and the height $δ_1$ of the rib top (8) refers to the height of the rib top (8) as projected in the axial direction of the reactor when the rib is installed in the reactor.

In one embodiment, the baffle component (1) has an angle of −25 to 60°, preferably −20 to 50°, more preferably −15 to 40°, with respect to the cross-section of the fluidized bed reaction zone.

The invention also provides a process for producing lower olefins, comprising the step of contacting an oxygenate feedstock with molecular sieve catalysts in a fluidized bed reaction zone, to generate a product of lower olefins under effective conditions; characterized in that in the fluidized bed reaction zone, the superficial gas velocity μ and the bed layer average catalyst density ρ are configured to satisfy the formula (I) below:

$$\rho=0.356\mu^3-4.319\mu^2-35.57\mu+M \quad (I)$$

wherein, M=250-554, preferably 300-550, or 400-500, such as 487.9; μ is provided in m/s and ρ is provided in kg/m³; or when the superficial gas velocity μ and the bed average catalyst density ρ do not satisfy formula (I), the superficial gas velocity is adjusted by the method according to aspect 1 or any other aspect of the invention so as to lead the superficial gas velocity μ and bed average catalyst density ρ to satisfying formula (I).

EXAMPLES

Example 1

Figure 1:
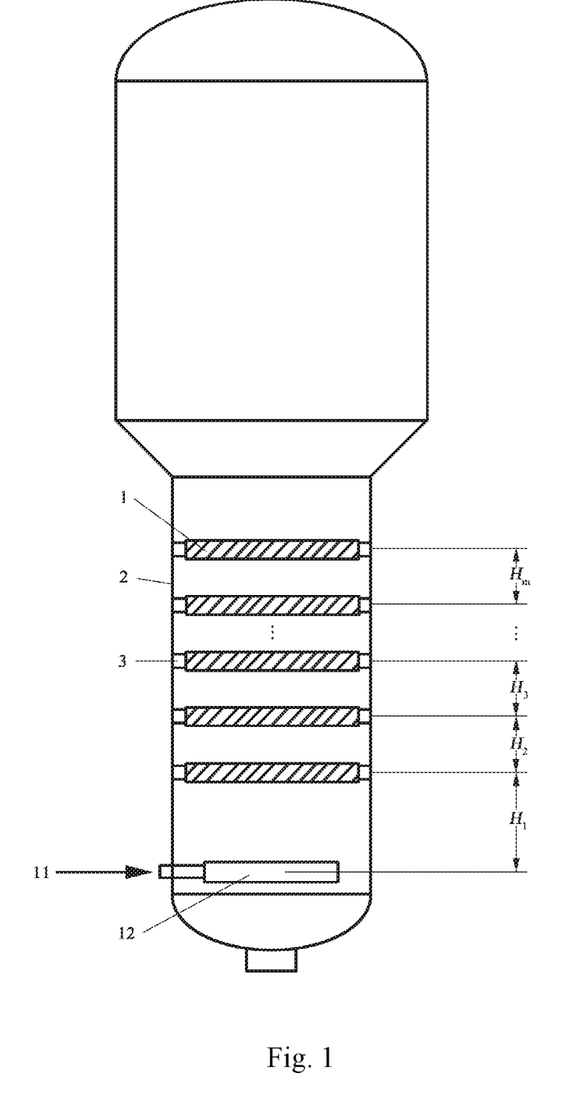
FIG. 1 illustrates a reactor for producing lower olefins using the process of the present invention.

A fluidized bed reactor was used, comprising a fluidized bed reaction zone using solid catalysts as fluidized particles, the bottom of the reaction zone being provided with a feed line (11) and a feed distribution plate (12), and the reaction zone of the fluidized bed being provided with a plurality of the baffle components $B_j$ (1) therein, where j=5. The baffle components (1) were fixed in the reaction area through brackets (3); the adjacent two layers of the baffle components $B_j$ (1) were staggered; the distance between the layers of the baffle components (1) was $H_j$, and the lowest baffle component $B_1$ (1) was arranged at a position spacing from the methanol feed distribution plate at a distance of $H_1$. The baffle component $B_j$ (1) comprised a plurality of rib plates (7), the rib plates (7) being in radial arrangement (A); and the arrangement of the plurality of rib plates (7) of each layer of the baffle components $B_j$ (1) was the same. The baffle components $B_j$ (1) in radial arrangement (A) comprised rib plates (7) and positioning rings $R_i$ (6); where the positioning rings $R_i$ (6) were coaxially arranged. The rib plates (7) were connected with the positioning rings $R_i$ (6) and were uniformly distributed along the circumferential direction, where the number of the positioning rings $R_i$ (6) was n, n was 3, and each layer of the positioning rings (6) was represented by i, i=1−n, wherein $R_1$ represented the radially innermost positioning ring, and Rn was the radially outermost positioning ring. The n positioning rings $R_i$ divided the reaction zone of the fluidized bed into n+1 rib plate ring layers $L_g$ which were coaxial in the radial direction, wherein g=1 to (n+1), where the 1st rib plate ring layer was the rib plate ring layer at the innermost side in the radial direction. The number of the rib plates (7) of each rib plate ring layer was p, the number of the rib plates (7) in the g-th rib plate ring layer $L_g$ was $p_g$, and $p_g$ was 5×g.

The rib plate (7) was in π-shape (D1). The rib plate (7) was provided with small holes (10); and the small holes (10) were in circle shape. The rib plate (6) in π-shape (D1) comprised a rib plate flank (9) and a rib plate top (8). The width l of the rib plate (7) was 0.5 times of (D−2×$h_1$)/p and the height δ of the rib plate (7) was 0.5 times of the width l of the rib plate (7). The width $l_i$ of the rib plate top (8) of the rib plate (6) in π-shape (D1) was 0.35 times of the width l of the rib plates (7); and the height $δ_1$ of the rib top (8) of the rib plate (6) in π-shape (D1) was 0.15 times of the height δ of the rib plate (7). The rib plate flank (9) of the rib plate (6) in π-shape (D1) was in an arc shape.

When the baffle component Bj (1) was projected on the cross section of the reaction zone of the fluidized bed, the cross section area not occupied by the projection accounted for 80% of the cross section area of the reaction zone of the fluidized bed. The ratio of $H_1$ to the height of the reaction zone was 0.25, and the ratio of $H_j$ to the diameter D of the reaction zone was 0.5. The distance between the outermost edge of the baffle component $B_j$ (1) and the reaction zone cylinder wall (2) of the fluidized bed was $h_1$, which was 0.01 times of the diameter D of the reaction zone of the fluidized bed. The angle of the baffle component B1 (1) to the cross-section of the fluidized bed reaction zone was 0°.

The superficial gas velocity μ of the fluidized bed reaction zone was measured, and compared with the bed average catalyst density ρ of the solid catalysts in the fluidized bed reaction zone, and the superficial gas velocity μ was adjusted as needed such that the superficial gas velocity μ and the bed average catalyst density ρ satisfied the formula (I) below:

$$\rho=0.356\mu^3-4.319\mu^2-35.57\mu+M \quad (I)$$

wherein M was a setpoint of 487.9, with a control range of 486-489;

μ was provided in m/s and p was provided in kg/m³.

The fluidized bed reactor was used for the reaction of producing olefins from methanol. The fluidized bed reactor was in a fast fluidized form, the methanol feedstock was fed at a scale of 2.4 million tons per year, the diameter of the reaction zone of the reactor was 8 m, the height of the reaction zone of the reactor was 10 m, and the operation was measured at a cycle of 7 days.

A stream comprising methanol feedstock (with purity of methanol of 95 wt %, and the remaining being mainly water) was fed into the reaction zone of the reactor through a feed line, and contacted with the molecular sieve catalysts for reaction, to generate a product containing lower olefins. The spent catalysts were carried into the separation zone of the reactor through the gas-solid rapid separation zone, wherein most of the catalysts separated by the gas-solid rapid separation device were fed to a steam stripping zone, while the gas-phase product and a part of the catalysts not separated by the gas-solid rapid separation device were fed to a cyclone to be separated further. The catalysts were returned to the steam stripping zone through the dipleg of the cyclone, and the gas-phase product was fed to a subsequent separation working section through a gas collection chamber and an outlet pipeline. The spent catalysts separated by the gas-solid rapid separation zone and the cyclone were divided into two parts after steam stripping, where one part was returned to the bottom of the reaction zone through a catalyst external circulation inclined line; and the other part was fed to the dense phase section of the regenerator through a spent inclined line to be regenerated by coke burning. Flue gas generated by coke burning was fed to a subsequent energy recovery system through a flue gas outlet line after passing through a cyclone, and the regenerated catalyst after regeneration was returned to the reaction zone through the spent inclined line to be regenerated.

The top pressure of the reactor was 0.2 MPa and the reaction temperature was 480° C. The average coke deposition amount of the catalysts was 3.5 wt %, the average bed density of the reaction zone was 426 kg/m³, and the superficial gas velocity was 1.5 m/s. The active component of the catalyst was silicoaluminophosphate molecular sieve, and the silicoaluminophosphate molecular sieve was SAPO-34.

The results of sampling analysis showed that the average carbon-based yield of ethylene+propylene at the reactor outlet was 82.71% during one operation cycle.

Example 2

The conditions and procedures described in Example 1 were followed except that: the arrangement of the rib plates (7) was spiral arrangement (B1), the angle between the tangent of the outer curvature of the rib plate (7) of the baffle component (1) in spiral arrangement (B1) and the radius direction was α, which was 30°. The baffle component $B_j$ (1) comprised a positioning ring $R_i$ (6), the rib plates (7) of two adjacent rib ring layers (i-th rib ring layer and (i+1)-th rib ring layer) of the baffle component (1) in spiral arrangement (B1) were arranged in the same direction.

The rib plate (7) was in π-shape (D3). The rib plate (7) was provided with small holes (10); and the small holes (10) were in ellipse shape. The width l of the rib plate (7) was 0.4 times of $(D-2\times h_i)/p$ and the height δ of the rib plate (7) was 0.4 times of the width l of the rib plate (7). The width $l_i$ of the rib plate top (8) of the rib plate (6) in π-shape (D3) was 0.2 times of the width l of the rib plates (7); and the height $δ_1$ of the rib top (8) of the rib plate (6) in π-shape (D3) was 0.1 times of the height δ of the rib plate (7).

The rib plate flank (9) of the rib plate (6) in π-shape (D3) was in a flat shape.

The average bed density of the reaction zone was 485 kg/m³, and the superficial gas velocity was 1.5 m/s.

Other conditions and procedures not specifically mentioned were the same as in Example 1.

The results of sampling analysis showed that the average carbon-based yield of ethylene+propylene at the reactor outlet was 83.02% during one operation cycle.

Example 3

The conditions and procedures described in Example 2 were followed, except that: the arrangement of ribbed plate (7) was spiral arrangement (B2), namely the rib plates (7) of two adjacent rib ring layers (i-th rib ring layer and (i+1)-th rib ring layer) of the baffle component (1) in spiral arrangement (B2) were arranged in the opposite directions.

The average bed density of the reaction zone was 474 kg/m³, and the superficial gas velocity was 1.5 m/s.

Other conditions and procedures not specifically mentioned were the same as in Example 2.

The results of sampling analysis showed that the average carbon-based yield of ethylene+propylene at the reactor outlet was 82.94% during one operation cycle.

Example 4

The conditions and procedures described in Example 2 were followed, except that: the angle between the tangent of the outer curvature of the rib plate (7) of the baffle component (1) in spiral arrangement (B1) and the radius direction was a, which was 60°.

The rib plate (7) was in arc shape (D7). The rib plate (7) was provided with small holes (10); and the small holes (10) were in circle shape. The width l of the rib plate (7) was 0.6 times of $(D-2\times h_1)/p$ and the height δ of the rib plate (7) was 0.5 times of the width l of the rib plate (7).

The average bed density of the reaction zone was 407 kg/m³, and the superficial gas velocity was 1.5 m/s.

Other conditions and procedures not specifically mentioned were the same as in Example 2.

The results of sampling analysis showed that the average carbon-based yield of ethylene+propylene at the reactor outlet was 82.01% during one operation cycle.

Example 5

The conditions and procedures described in Example 1 were followed except that: the methanol feeding scale was 3 million tons per year, the diameter of the reaction zone of the reactor was 8 m, the top pressure of the reactor was 0.3 MPa and the reaction temperature was 500, the average coke deposition amount of the catalysts was 4.0 wt %, the average bed density of the reaction zone was 454 kg/m³, and the superficial gas velocity was 2.5 m/s.

Other conditions and procedures not specifically mentioned were the same as in Example 1.

The results of sampling analysis showed that the average carbon-based yield of ethylene+propylene at the reactor outlet was 81.87% during one operation cycle.

Example 6

The conditions and procedures described in Example 1 were followed except that: the methanol feeding scale was 3 million tons per year, the diameter of the reaction zone of the reactor was 8 m, the top pressure of the reactor was 0.3 MPa and the reaction temperature was 500° C., the average coke deposition amount of the catalysts was 4.0 wt %, the average bed density of the reaction zone was 397 kg/m³, and the superficial gas velocity was 2.5 m/s.

Other conditions and procedures not specifically mentioned were the same as in Example 1.

The results of sampling analysis showed that the average carbon-based yield of ethylene+propylene at the reactor outlet was 81.45% during one operation cycle.

Example 7

The conditions and procedures described in Example 1 were followed except that: the average coke deposition amount of the catalysts was 4.0 wt %, the average bed density of the reaction zone was 355 kg/m³, and the superficial gas velocity was 3 m/s.

Other conditions and procedures not specifically mentioned were the same as in Example 1.

The results of sampling analysis showed that the average carbon-based yield of ethylene+propylene at the reactor outlet was 81.36% during one operation cycle.

Example 8

The conditions and procedures described in Example 1 were followed except that: the average coke deposition amount of the catalysts was 4.0 wt %, the average bed density of the reaction zone was 505 kg/m³, and the superficial gas velocity was 1.0 m/s.

Other conditions and procedures not specifically mentioned were the same as in Example 1.

The results of sampling analysis showed that the average carbon-based yield of ethylene+propylene at the reactor outlet was 83.05% during one operation cycle.

Example 9

The conditions and procedures described in Example 1 were followed except that: the methanol feeding scale was 1.8 million tons per year, the average coke deposition amount of the catalysts was 3.0 wt %, the average bed density of the reaction zone was 450 kg/m$^3$, and the superficial gas velocity was 1.15 m/s.

Other conditions and procedures not specifically mentioned were the same as in Example 1.

The results of sampling analysis showed that the average carbon-based yield of ethylene+propylene at the reactor outlet was 83.14% during one operation cycle.

Example 10

The conditions and procedures described in Example 1 were followed except that: the number of the rib plates (7) of each rib plate ring layer was p, the number of the rib plates (7) in the g-th rib plate ring layer was $p_g$, and $p_g$ was 8×g. The width l of the rib plate (7) was 0.8 times of (D−2×h$_1$)/p and the height δ of the rib plate (7) was 0.2 times of the width l of the rib plate (7). The width $l_1$ of the rib plate top (8) of the rib plate (6) in π-shape (D1) was 0.45 times of the width l of the rib plates (7); and the height $δ_1$ of the rib top (8) of the rib plate (6) in π-shape (D1) was 0.2 times of the height δ of the rib plate (7).

When the baffle component $B_j$ (1) was projected on the cross section of the reaction zone of the fluidized bed, the cross section not occupied by the projection accounted for 83% of the cross section area of the reaction zone of the fluidized bed. The ratio of $H_1$ to the height of the reaction zone was 0.25, and the ratio of $H_j$ to the diameter of the reaction zone was 0.4. The distance between the outermost edge of the baffle component $B_j$ (1) and the reaction zone cylinder wall (2) of the fluidized bed was $h_1$, which was 0.02 times of the diameter D of the reaction zone of the fluidized bed. The angle of the baffle component B1 (1) to the cross-section of the fluidized bed reaction zone was −10°.

The average bed density of the reaction zone was 447 kg/m$^3$, and the superficial gas velocity was 1.5 m/s.

Other conditions and procedures not specifically mentioned were the same as in Example 1.

The results of sampling analysis showed that the average carbon-based yield of ethylene+propylene at the reactor outlet was 82.82% during one operation cycle.

Example 11

The conditions and procedures described in Example 1 were followed except that: when the baffle component $B_j$ (1) was projected on the cross section of the reaction zone of the fluidized bed, the cross section not occupied by the projection accounted for 75% of the cross section area of the reaction zone of the fluidized bed. The ratio of $H_1$ to the height of the reaction zone was 0.25, and the ratio of $H_j$ to the diameter of the reaction zone was 0.7. The distance between the outermost edge of the baffle component $B_j$ (1) and the reaction zone cylinder wall (2) of the fluidized bed was $h_1$, which was 0.03 times of the diameter D of the reaction zone of the fluidized bed. The angle of the baffle component B1 (1) to the cross-section of the fluidized bed reaction zone was 20°.

The average bed density of the reaction zone was 410 kg/m$^3$, and the superficial gas velocity was 1.5 m/s.

Other conditions and procedures not specifically mentioned were the same as in Example 1.

The results of sampling analysis showed that the average carbon-based yield of ethylene+propylene at the reactor outlet was 82.33% during one operation cycle.

Example 12

The conditions and procedures described in Example 1 were followed, the reaction zone of the fluidized bed being provided with a plurality of the baffle components $B_j$ (1) therein, where j=3; and the rib plates (7) were in dendritic arrangement (C1).

The baffle components $B_j$ (1) in dendritic arrangement (C1) had rib plates (7) consisting of main rib plates (4) and auxiliary rib plates (5). The number of the main rib plates (4) was k, k being 4. The main rib plates (4) and the auxiliary rib plates (5) were perpendicularly arranged in a crossed manner and were in a dendritic shape. The number of auxiliary rib plates (5) on each baffle component $B_j$ (1) was q, q being 30. The main rib plates (4) of the baffle component (1) were arranged in parallel, and had different lengths and the same spacing distance. The auxiliary rib plates (5) on each main rib plate (4) had different quantity, were arranged in parallel, and had the same spacing distance. The auxiliary rib plates (5) on interval main rib plates (4) were aligned; and the spacing $h_3$ of every two adjacent auxiliary rib plates (5) on the interval main rib plates (4) was 0.1 times of (D−2×h$_1$)/k.

When the baffle component $B_j$ (1) was projected on the cross section of the reaction zone of the fluidized bed, the cross section not occupied by the projection accounted for 75% of the cross section area of the reaction zone of the fluidized bed. The ratio of $H_1$ to the height of the reaction zone was 0.15, and the ratio of $H_j$ to the diameter of the reaction zone was 0.5. The distance between the outermost edge of the baffle component $B_j$ (1) and the reaction zone cylinder wall (2) of the fluidized bed was $h_1$, which was 0.05 times of the diameter D of the reaction zone of the fluidized bed. The angle of the baffle component B1 (1) to the cross-section of the fluidized bed reaction zone was 0°.

The average bed density of the reaction zone was 382 kg/m$^3$, and the superficial gas velocity was 1.5 m/s.

Other conditions and procedures not specifically mentioned were the same as in Example 1.

The results of sampling analysis showed that the average carbon-based yield of ethylene+propylene at the reactor outlet was 81.03% during one operation cycle.

Example 13

The conditions and procedures described in Example 1 were followed, the reaction zone of the fluidized bed being provided with a plurality of the baffle components $B_j$ (1) therein, where j=3; and the rib plates (7) were in dendritic arrangement (C2).

The baffle components $B_j$ (1) in dendritic arrangement (C2) had rib plates (7) consisting of main rib plates (4) and auxiliary rib plates (5). The number of the main rib plates (4) was k, k being 4. The main rib plates (4) and the auxiliary rib plates (5) were perpendicularly arranged in a crossed manner and were in a dendritic shape. The number of auxiliary rib plates (5) on each baffle component $B_j$ (1) was q, q being 30. The main rib plates (4) of the baffle component (1) were arranged in cross, and had a length of D−2×h$_1$. The auxiliary rib plates (5) on each main rib plate (4) had the same quantity. The auxiliary rib plates (5) on each main rib plate (4) formed sector areas, and the distance $h_6$ between the sector areas was 1 time of $h_1$. The auxiliary rib plates (5)

on each main rib plate (4) were arranged parallel to each other and had the same spacing $h_5$.

When the baffle component $B_j$ (1) was projected on the cross section of the reaction zone of the fluidized bed, the cross section not occupied by the projection accounted for 78% of the cross section area of the reaction zone of the fluidized bed. The ratio of $H_1$ to the height of the reaction zone was 0.25, and the ratio of $H_j$ to the diameter D of the reaction zone was 0.5. The distance between the outermost edge of the baffle component $B_j$ (1) and the reaction zone cylinder wall (2) of the fluidized bed was $h_1$, which was 0.04 times of the diameter D of the reaction zone of the fluidized bed. The angle of the baffle component B1 (1) to the cross-section of the fluidized bed reaction zone was 0°.

The average bed density of the reaction zone was 400 kg/m³, and the superficial gas velocity was 1.5 m/s.

Other conditions and procedures not specifically mentioned were the same as in Example 1.

The results of sampling analysis showed that the average carbon-based yield of ethylene+propylene at the reactor outlet was 81.25% during one operation cycle.

Example 14

The conditions and procedures described in Example 1 were followed, the reaction zone of the fluidized bed being provided with a plurality of the baffle components $B_j$ (1) therein, where j=3; and the rib plates (7) were in dendritic arrangement (C3).

The baffle components $B_j$ (1) in dendritic arrangement (C3) had rib plates (7) consisting of main rib plates (4) and auxiliary rib plates (5). The number of the main rib plates (4) was k, k being 8. The main rib plates (4) and the auxiliary rib plates (5) were perpendicularly arranged in a crossed manner and were in a dendritic shape. The number of auxiliary rib plates (5) on each baffle component $B_j$ (1) was q, q being 36. The main rib plates (4) of the baffle component (1) were arranged in cross, and had a length of D−2×$h_1$. The auxiliary rib plates (5) on each main rib plate (4) had the same quantity. The auxiliary rib plates (5) on each main rib plate (4) formed sector areas, and the distance $h_6$ between the sector areas was 1 time of $h_1$. The auxiliary rib plates (5) on each main rib plate (4) were arranged parallel to each other and had the same spacing $h_5$.

When the baffle component $B_j$ (1) was projected on the cross section of the reaction zone of the fluidized bed, the cross section not occupied by the projection accounted for 82% of the cross section area of the reaction zone of the fluidized bed. The ratio of $H_1$ to the height of the reaction zone was 0.25, and the ratio of $H_j$ to the diameter of the reaction zone was 0.5. The distance between the outermost edge of the baffle component $B_j$ (1) and the reaction zone cylinder wall (2) of the fluidized bed was $h_1$, which was 0.04 times of the diameter D of the reaction zone of the fluidized bed. The angle of the baffle component B1 (1) to the cross-section of the fluidized bed reaction zone was 0°.

The average bed density of the reaction zone was 417 kg/m³, and the superficial gas velocity was 1.5 m/s.

Other conditions and procedures not specifically mentioned were the same as in Example 1.

The results of sampling analysis showed that the average carbon-based yield of ethylene+propylene at the reactor outlet was 81.67% during one operation cycle.

Example 15

The conditions and procedures described in Example 14 were followed, and the rib plates (7) were in 7C arrangement (D3). The rib plate (7) was provided with small holes (10); and the small holes (10) were in ellipse shape. The width l of the rib plate (7) was 0.4 times of (D−2×$h_1$)/p and the height δ of the rib plate (7) was 0.4 times of the width l of the rib plate (7). The width $l_i$ of the rib plate top (8) of the rib plate (6) in π-shape (D3) was 0.2 times of the width l of the rib plates (7); and the height $δ_1$ of the rib top (8) of the rib plate (6) in π-shape (D3) was 0.1 times of the height δ of the rib plate (7). The rib plate flank (9) of the rib plate (6) in π-shape (D1) was in a flat shape.

The average bed density of the reaction zone was 390 kg/m³, and the superficial gas velocity was 1.5 m/s.

Other conditions and procedures not specifically mentioned were the same as in Example 14.

The results of sampling analysis showed that the average carbon-based yield of ethylene+propylene at the reactor outlet was 81.22% during one operation cycle.

Example 16

The conditions and procedures described in Example 14 were followed, and the rib plates (7) were in arc arrangement (D7). The rib plate (7) was provided with small holes (10); and the small holes (10) were in circle shape. The width l of the rib plate (7) was 0.6 times of (D−2×$h_1$)/p and the height δ of the rib plate (7) was 0.5 times of the width l of the rib plate (7).

The average bed density of the reaction zone was 375 kg/m³, and the superficial gas velocity was 1.5 m/s.

Other conditions and procedures not specifically mentioned were the same as in Example 14.

The results of sampling analysis showed that the average carbon-based yield of ethylene+propylene at the reactor outlet was 81.03% during one operation cycle.

Example 17

The conditions and procedures described in Example 1 were followed, except that the silicoaluminophosphate molecular sieve was SAPO-18.

Other conditions and procedures not specifically mentioned were the same as in Example 1.

The results of sampling analysis showed that the average carbon-based yield of ethylene+propylene at the reactor outlet was 81.54% during one operation cycle.

Comparative Example 1

The conditions and procedures described in Example 1 were followed, except that no baffle was installed in the reaction zone. The average coke deposition amount of the catalysts was 4.0 wt %, the average bed density of the reaction zone was 120 kg/m³, and the superficial gas velocity was 1.5 m/s.

Other conditions and procedures not specifically mentioned were the same as in Example 1.

The results of sampling analysis showed that the average carbon-based yield of ethylene+propylene at the reactor outlet was 80.07% during one operation cycle.

Comparative Example 2

The conditions and procedures described in Comparative Example 1 were followed, with the same reactor dimension, but the methanol feeding scale was increased to 2.4 million tons per year, and no baffle was installed in the reaction zone. The average coke deposition amount of the catalysts was 4.2 wt %, the average bed density of the reaction zone was 90 kg/m³, and the superficial gas velocity was 2 m/s.

Other conditions in comparison with procedures not specifically mentioned were the same as in Comparative Example 1.

The results of sampling analysis showed that the average carbon-based yield of ethylene+propylene at the reactor outlet was 79.57% during one operation cycle.

Comparative Example 3

The conditions and procedures described in Comparative Example 1 were followed, with the same reactor dimension, but the methanol feeding scale was increased to 3 million tons per year, and no baffle was installed in the reaction zone. The average coke deposition amount of the catalysts was 4.5 wt %, the average bed density of the reaction zone was 60 kg/m³, and the superficial gas velocity was 2.5 m/s.

Other conditions in comparison with procedures not specifically mentioned were the same as in Comparative Example 1.

The results of sampling analysis showed that the average carbon-based yield of ethylene+propylene at the reactor outlet was 75.34% during one operation cycle.

Comparative Example 4

The conditions and procedures described in Example 5 were followed, except that no baffle was installed in the reaction zone. The average coke deposition amount of the catalysts was 5 wt %, the average bed density of the reaction zone was 30 kg/m³, and the superficial gas velocity was 2 m/s.

Other conditions and procedures not specifically mentioned were the same as in Example 5.

The results of sampling analysis showed that the average carbon-based yield of ethylene+propylene at the reactor outlet was 72.09% during one operation cycle.

Comparative Example 5

The conditions and procedures described in Example 5 were followed, except that no baffle was installed in the reaction zone. The average coke deposition amount of the catalysts was 5 wt %, the average bed density of the reaction zone was 30 kg/m³, and the superficial gas velocity was 2 m/s.

Other conditions and procedures not specifically mentioned were the same as in Example 5.

The results of sampling analysis showed that the average carbon-based yield of ethylene+propylene at the reactor outlet was 72.09% during one operation cycle.

Obviously, the process according to the present invention could achieve the purpose of improving the yield of the lower olefins showing great technical advantages, and thus was able to be used for the industrial production of the lower olefins.

The invention claimed is:

1. A method for regulating the superficial gas velocity in a fluidized bed, wherein solid catalysts are used as fluidized particles or as a part of the fluidized particles, characterized in measuring the superficial gas velocity u of the reaction zone of the fluidized bed, comparing it with the bed average catalyst density p of the solid catalysts in the reaction zone of the fluidized bed, adjusting the superficial gas velocity u as needed so as to allow the superficial gas velocity u and the bed average catalyst density p satisfy the formula (I) below:

$$\rho = 0.356\mu^3 - 4.319\mu^2 - 35.57\mu + M \quad (I)$$

wherein M=250-554;

μ is provided in m/s and p is provided in kg/m³.

2. The method according to claim 1, wherein the bed average catalyst density is 200 to 500 kg/m³.

3. The method according to claim 1, wherein baffle components $B_j$ are provided within the reaction zone of the fluidized bed, the number of layers of the baffle components being independently in each case m, m being a value varying between 2 and 50; and the distance between two adjacent baffle components $B_j$ is $H_j$, except $H_1$, each $H_j$ other than $H_1$ being independently 0.2-1 times of the diameter D of the fluidized bed reaction zone, wherein j=1–m;

the baffle component $B_j$ comprises a plurality of rib plates, and the arrangement of the rib plates is one of radial arrangement (A), spiral arrangement (B1-B2) and dendritic arrangement (C1-C3);

when the baffle component $B_j$ is projected on the cross section of the reaction zone of the fluidized bed, the cross section area not occupied by the projection accounts for 70-95% of the cross section area of the reaction zone of the fluidized bed; and the distance between the outermost edge of any baffle component $B_j$ and the reaction zone cylinder wall of the fluidized bed is each $h_1$; and $h_1$ is independently 0.005 to 0.05 times of the diameter D of the reaction zone of the fluidized bed.

4. The method according to claim 3, wherein baffle components $B_j$ in radial arrangement (A) or spiral arrangement (B1-B2) comprise rib plates and positioning rings $R_i$; the positioning rings $R_i$ are coaxially arranged; the rib plates are connected with the positioning rings $R_i$ and are uniformly distributed along the circumferential direction, wherein:

(a) the number of the positioning rings $R_i$ is n independently, wherein n is a value varying from 1 to 10, and i=1 to n; and the n positioning rings $R_i$ divide the reaction zone of the fluidized bed into n+1 rib plate ring layers which are coaxial in the radial direction, each rib plate ring layer being represented by $L_g$, and g=1 to (n+1); and (b) the number of the rib plates of each rib plate ring layer is p, the number of the rib plates in the g-th rib plate ring layer $L_g$ is $p_g$, and the range for $p_g$ is (3–10)×g.

5. The method according to claim 3, wherein the baffle components in spiral arrangement (B1-B2) has an angle α between the tangent of the outer curvature of the rib plate and the radial direction, α being 10-80°.

6. The method according to claim 3, wherein the baffle components $B_j$ in dendritic arrangement (C1-C3) are formed of a plurality of main rib plates and a plurality of auxiliary rib plates; the number of the main rib plates on each baffle component $B_j$ is k independently, and k is 2-8; the main rib plates and the auxiliary rib plates are perpendicularly arranged in a crossed manner; and the total number of the auxiliary rib plates on each baffle component $B_j$ is q independently, and q is 10-40.

7. The method according to claim 6, wherein the baffle component Bj in dendritic arrangement has a type I dendritic arrangement (C1) in which two of the plurality of the main rib plates are each D–2×$h_1$ in length and are perpendicular to each other, which are referred to as a first main rib plate and a perpendicular main rib plate, respectively; the other main rib plates in the plurality of main rib plates are arranged in parallel with the first main rib plate, with a same spacing distance $h_4$; the auxiliary rib plates on each main rib plate are arranged in parallel, with a same spacing distances $h_2$; a pair of auxiliary rib plates on the first main rib plate, which are closest to the perpendicular main rib plate, are respectively spacing from the perpendicular main rib plate by a distance $h_2$, a pair of auxiliary rib plates on two main rib plates adjacent to the first main rib plate, which are respectively closest to the perpendicular main rib plate, are respectively spacing from the perpendicular main rib plate by a distance ½$h_2$, and the auxiliary rib plates on the interval main rib plates are aligned on a straight line in the longitudinal direction; and the distance $h_3$ between the ends of the auxiliary rib plates on the interval main rib plates is (0.01-0.2) times of $(D-2\times h_1)/k$.

8. The method according to claim 6, wherein the baffle component $B_j$ in dendritic arrangement has a type II dendritic arrangement (C2-C3), wherein the main rib plates of the baffle components are arranged crosswise and uniformly arranged circumferentially with a length of $D-2\times h_1$; the number of the auxiliary rib plates on each main rib plate is the same, the auxiliary rib plates are arranged in parallel with a same spacing distance $h_5$; the auxiliary rib plates on each main rib plate form sector areas, and the distance $h_6$ between the sector areas is 0.5-3 times of $h_1$.

9. The method according to claim 3, wherein the rib plate is in any one of π-shape, inverted V-shape, inclined plate-shape and arc-shape; the rib plate is provided with small holes; the small holes are in any one of circle, ellipse, rectangle, triangle, polygon and the like shape; and the rib plate in π-shape comprises a rib plate flank and a rib plate top.

10. The method according to claim 9, wherein the width l of the rib plate is (0.2-0.9) times of $(D-2\times h_1)/(p$ or $q)$ and the height δ of the rib plate is (0.1-0.6) times of the width l of the rib plate.

11. The method according to claim 9, wherein the width l1 of the rib plate top of the rib plate in π-shape is (0.1-0.5) times of the width l of the rib plates; the height $δ_1$ of the rib top of the rib plate in π-shape is 0.05-0.3 times of the height δ of the rib plate.

12. The method according to claim 3, wherein the angle of the baffle component to the cross-section of the fluidized bed reaction zone is from −25 to 60°.

13. The method according to claim 3, wherein the angle of the baffle component to the cross-section of the fluidized bed reaction zone is from −15 to 40°.

14. The method according to claim 1, wherein the bed average catalyst density is 300 to 430 kg/m³.

15. The method according to claim 1, wherein m is a value varying between 2 and 20.

16. The method according to claim 1, wherein m is a value varying between 2 and 10.

17. The method according to claim 1, comprising providing a control value M' for a control range within ±5% from a setpoint value of M, wherein when no control value M' is present within the control range of the setpoint value M such that the superficial gas velocity μ and the bed density p satisfy the formula (I), the setpoint value M is brought into the formula, a calculated value of the corresponding superficial gas velocity μ is calculated from the bed density p accordingly, and the superficial gas velocity is adjusted in accordance with the calculated value.

18. A process for producing lower olefins, comprising the step of contacting an oxygenate feedstock with molecular sieve catalysts in a fluidized bed reaction zone, to generate lower olefins under effective conditions; wherein in the fluidized bed reaction zone, the superficial gas velocity μ and the bed average catalyst density p are allowed to satisfy the formula (I) below:

$$\rho=0.356\mu^3-4.319\mu^2-35.57\mu+M \quad \text{(I)};$$

wherein, M=250-554;

μ is provided in m/s and p is provided in kg/m³; or when the superficial gas velocity μ and the bed average catalyst density p do not satisfy formula (I), the superficial gas velocity is adjusted by the method according to claim 1 so as to lead the superficial gas velocity μ and bed average catalyst density p to satisfying formula (I).

19. The process for producing lower olefins according to claim 18, wherein the effective conditions comprise: a top pressure of the reactor of more than 0.1 MPa; a reaction temperature of more than 400.

20. The process for producing lower olefins according to claim 18, wherein the oxygenate feedstock comprises methanol; the molecular sieve is a silicoaluminophosphate molecular sieve.

* * * * *